(12) United States Patent
Kapel et al.

(10) Patent No.: US 9,095,595 B2
(45) Date of Patent: Aug. 4, 2015

(54) COMPOSITION COMPRISING PARASITE EGGS AND METHODS FOR ISOLATION AND STORAGE OF PARASITE EGGS

(75) Inventors: Christian Mollin Outzen Kapel, Rungsted Kyst (DK); Allan Roepstorff, Rødovre (DK); Stig Milan Thamsborg, Gentofte (DK)

(73) Assignee: Parasite Technologies A/S, Rungsted Kyst (DK)

( * ) Notice: Subject to any disclaimer, the term of this patent is extended or adjusted under 35 U.S.C. 154(b) by 181 days.

(21) Appl. No.: 13/331,249

(22) Filed: Dec. 20, 2011

(65) Prior Publication Data

US 2012/0085286 A1 Apr. 12, 2012

Related U.S. Application Data

(63) Continuation of application No. 12/142,474, filed on Jun. 19, 2008, now abandoned, which is a continuation of application No. 12/158,207, filed on Nov. 18, 2008, now abandoned.

(51) Int. Cl.
| | |
|---|---|
| *A61K 35/56* | (2006.01) |
| *C12N 1/04* | (2006.01) |
| *A61K 35/62* | (2006.01) |
| *C12N 5/07* | (2010.01) |

(52) U.S. Cl.
CPC .............. *A61K 35/62* (2013.01); *C12N 5/0601* (2013.01)

(58) Field of Classification Search
None
See application file for complete search history.

(56) References Cited

U.S. PATENT DOCUMENTS

| | | | | |
|---|---|---|---|---|
| 5,989,595 | A * | 11/1999 | Cummins | 424/710 |
| 6,242,011 | B1 * | 6/2001 | Cummins | 424/710 |
| 6,468,430 | B1 * | 10/2002 | Kimura et al. | 210/636 |
| 6,764,838 | B2 * | 7/2004 | Weinstock et al. | 435/71.1 |

OTHER PUBLICATIONS

Pedersen et al. Parasitology (2001), 123, 95-101.*
The Engineering ToolBox (www.enginerringtoolbox.com/acids-ph-d_401.html) p. 1-5, retrieved Aug. 28, 2010.*
Trichuriasis FactSheet Spicker, Anna Rovid. Trichuriasis, last updated May 2005 (www.cfsph.iastate.edu/Factsheets/pdfs/trichuriasis.pdf).*
Ichhpujani et al (Medical Parasitology 3rd edition, Jaypee Brother Medical Publishers Ltd, India).*
Nelson et al. Applied and Environmental Biology. vol. 67, No. 12, p. 5453-5459, Dec. 2001.*
Nelson et al. Applied and Environmental Microbiology, Dec. 2001, p. 5452-5459.*
Arene et al. J. Term. biol. vol. 11, No. 1, p. 9-15, 1986.*
Ascarias lumbricoides. Web Atlas of Medical Parasitology. Retrieved online Feb. 3, 2012.*
Levine, P.P. Infection of the Chicken with *Capillaria* Columbaie (Rud). Cited by Applicants in Reply to Office Action for U.S. Appl. No. 13/046,062, the reply with receipt date Jun. 21, 2012. Date of publication not provided.*
Despommier, Dickson. Clin. Microbiol. Rev. 2003, 16(2):265-272, 2003.*

* cited by examiner

*Primary Examiner* — Oluwatosin Ogunbiyi
(74) *Attorney, Agent, or Firm* — K. David Crockett, Esq.; Niky Economy Syrengelas, Esq.; Crockett & Crockett, PC

(57) ABSTRACT

The invention relates to a composition for storage and development of eggs from helminthic parasites, where the composition further comprises a liquid carrier having a pH value of below 7 at a temperature of from 10C to ambient temperature. The liquid carrier can be sulphuric acid, $H_2SO_4$ with a pH in the range of from 0 to 2, and antibiotics can be added. The invention further relates to a method for treating, ameliorating, prophylactic or curative, an autoimmune or allergic disease in an individual, animal or man, using eggs being separated from the composition. The present invention also relates to methods for isolation, embryonation and preservation of eggs of helminthic parasite, and to a method for producing a pharmaceutical composition comprising a helminthic parasite preparation. The helminthic parasite eggs may be from the pig whipworm; *Trichuris suis* ova (TSO).

21 Claims, 4 Drawing Sheets

Figure 1:
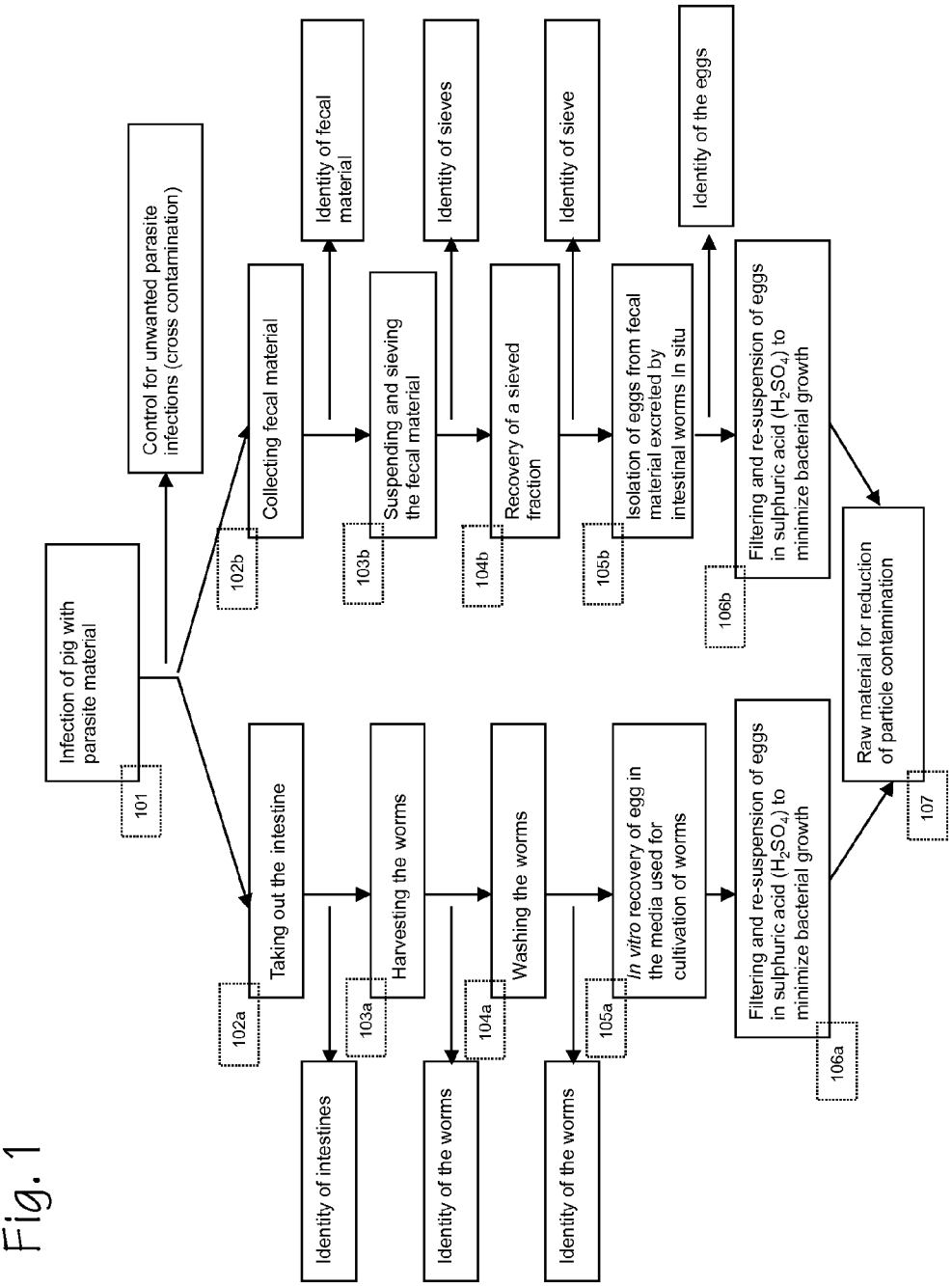

COMPOSITION COMPRISING PARASITE EGGS AND METHODS FOR ISOLATION AND STORAGE OF PARASITE EGGS

This application is a continuation of U.S. application Ser. No. 12/142,474, filed Jun. 19, 2008, now abandoned, which is a continuation of U.S. application Ser. No. 12/158,207 filed Nov. 18, 2008, now abandoned, which is the National Stage of International Application No. PCT/DK2006/000751, filed Dec. 29, 2006, which claims the benefit of DK PA 2005 01858, filed Dec. 30, 2005.

FIELD OF THE INVENTION

The present invention relates to a composition comprising eggs from a helminthic parasite and a method for treating, ameliorating, prophylactic or curative, an autoimmune or allergic disease in an individual animal or man using eggs being separated from the composition. The present invention further relates to methods for isolation and storage of eggs of a helminthic parasite, and to a method for producing a pharmaceutical composition comprising a helminthic parasite preparation. The helminthic parasite eggs may be from the pig whipworm; *Trichuris suis* ova (TSO).

BACKGROUND

TSO is the raw material of an active pharmaceutical ingredient, intended for treatment of autoimmune or allergic diseases.

The use of parasite material for medical treatment of inflammatory bowel disease (IBD) is described e.g. in U.S. Pat. No. 6,764,838.

The cause of inflammatory bowel disease (IBD) appears to involve both genetic and environmental factors. Current theories suggest that IBD results from an abnormal immune response to intestinal bacteria, initiated by unknown causes. IBD is common in industrialized countries where helminthic colonization is rare. Conversely, it is rare in regions of the world where most people have worms. Helminths could be beneficial in many autoimmune or allergic diseases because of their unique capacity to decrease hyper-reactive immune responses. In support of this idea, helminths reduce intestinal inflammation in both mice and man.

Members of helminth genus *Trichuris* are intestinal round worms (whipworms) with favorable characteristics for therapeutic use. *Trichuris suis*, the porcine whipworm, is genetically related to *Trichuris trichiura*, the human whipworm, but it has been shown experimentally to colonize humans only briefly without causing disease. The ova of *T. suis* can be produced using specific pathogen-free pigs, i.e. pigs free of infections with specified pathogens, and processed to assure absence of biological contaminants. For any production of TSO there are strict tolerances regarding the particle contamination and microbial activity of the solution used as a media:

1) The isolation process should ensure a particle contamination of the solution beyond 2% or 1% counted as numbers.

2) The isolation process should ensure that other parasite eggs are eliminated.

3) The microbial profile should fulfill the requirements for an oral administration containing raw material of natural origin under category 3B of the European Pharmacopoeia.

4) The media used for the storage should allow the development of the egg from un-embryonated (non-infective) to embryonated (infective) eggs.

5) The media should preferably not hold antibiotics or other chemicals, which may cause allergic reactions in potential patient.

6) The media used for the storage should allow for further long time storage (3-5 yrs) without affecting the infectivity of the TSO to facilitate an extended shelf life of a medicinal product.

7) The method should be applicable for the high quantity recovery of eggs.

DISCLOSURE OF THE INVENTION

Helminthic Parasites

In defining a helminthic parasite, there are two groups. The first group is helminthic parasites that naturally colonize specified mammalian hosts, including humans, and the second group is helminthic parasites that do not successfully colonize the specified mammalian species, including man, but may afford protection to an individual if they become infected, due to stimulation of the immune system.

In the first group, helminthic parasites are multi-cellular worms with complex life cycles and development adjusted to the specific mammalian species. The nematodes (non-segmented round worms) and the platyhelminths (flat worms) are two groups of helminths that may colonize the human intestines. In accordance with the present invention, any one of a number of helminthic parasites that naturally colonize humans or animals will provide the intended results. Nematodes that frequently inhabit the human gut are *Ascaris lumbricoides, Enterobius vermicularis* (pin worm), *Trichuris trichiura* (whipworm), *Ancylostoma duodenale* and *Necator americanus* (hookworms), and *Strongyloides stercoralis*. *Trichinella spiralis* infests the small intestine briefly but is rare.

The platyhelminths include the trematodes and cestodes. The most common adult trematodes that reside in the human intestines are *Fasciolopsis, Echinostoma* and *Heterophyes* species. Those that live in the biliary system include *Clonorchis sinensis, Opisthorchis viverini, O. felineus*, and *Fasciola hepatica* and *gigantica*. *Schistosoma* species dwell in the venous system, but several species chronically affect the gut by the passage of eggs through the intestinal wall. Adult cestodes commonly infecting humans are *Diphyllobothrium* species (fish tapeworm), *Taenia saginata* (beef tapeworm), *Taenia solium* (pork tapeworm) and *Hymenolepsis diminuta* and *H. nana* (dwarf tapeworm).

Other helminths of interest include the filarial parasites and the lung flukes. These do not have a gut phase, but stimulate strong immune responses (Th2-type).

The second general group of helminthic parasites that can be utilized in the present invention include helminths that normally do not colonize the specified mammalian species, including man, but may afford protection against diseases including allergies which are characterised by a "Th1-type" immune response. These include *Trichuris muris* (mouse whipworm), *Trichinella spiralis, Nippostrongylus brasiliensis, Heligmosomoides polygyrus* and *Hymenolepsis nana*, all of which are intestinal helminths infective to mice. *Trichuris suis* and *Ascaris suum* are pig helminths that can infect humans. *Trichuris vulpis, Toxocara* species, *Toxascaris* species, *Gnathostoma* species, and *Ancylostoma* species are dog or cat helminths that also can infect humans. *Anisakis* and *Pseudoterranova* are nematodes of marine mammals that can be transmitted to humans. Bird schistosomes can transiently infect humans. Such schistosomes include *S. douthitti, Trichobilharzia ocellata, T. stagnicolae, T. physellae*, and *Gigantobilharzia huronensis*.

Diseases Treatable Relevant to the Invention

A. Inflammatory Bowel Diseases (Crohn's Disease, CD, and Ulcerative Colitis, UC):

Epidemiological data suggest genetic susceptibility to the development of Crohn's disease (CD) and ulcerative colitis (UC). The incidence of CD in industrialized societies has increased from the 1950s and now is from 1 to 8 per 100,000 persons per year. This suggests that unknown changes in our environment have affected the frequency of CD.

While the cause of IBD remains undetermined, it is presumed to result from dysregulation of the intestinal mucosal immune system. Inflammatory cells in the mucosa normally protect us from luminal contents. This highly effective chronic inflammation is tightly controlled to limit tissue injury. IBD may result from inappropriately vigorous immune responses to luminal factors. CD appears to be an overly vigorous Th1-type inflammation that produces IFN-gamma and TNF-alpha. The nature of UC is less well defined.

There are several animal models of chronic intestinal inflammation. An important advance is the recent discovery that some mice with genetically engineered gene deletions can develop chronic bowel inflammation similar to IBD. These include mutant mice bearing targeted deletions for IL-2, IL-10, MHC class II or TCR genes among others. Using some of these models has shown that a dysregulated immune system itself can mediate intestinal injury. The mucosal inflammation of several of these models generates large amounts of IFN-gamma and TNF-alpha suggesting that excess production of Th1-type cytokines is one common mechanism underlying the pathogenesis of disease. Also, blocking Th1 circuitry prevents the inflammation. CD is also characterised by a high Th1 response. Thus, these models may have direct implications regarding the understanding of the immunopathology of this human disease process.

B. Rheumatoid Arthritis (RA):

RA is a chronic disease featuring persistent inflammatory synovitis, usually involving peripheral joints in a symmetric distribution. This inflammation can lead to bone erosions, cartilage damage and joint destruction. It is an affliction of about 1% of the population. The prevalence increases with age, and women are affected more frequently than men. The propagation of RA is an immunologically mediated event driven by CD4+ Th1 cells (type III hypersensitivity).

C. Insulin-Dependent, Juvenile Diabetes Mellitus (DM) (Type 1):

Type 1 DM is a disease that usually begins during early adulthood and that results from the inability to produce insulin in response to an increasing blood sugar concentration. Lac in insulin results in persistent high blood sugar levels and inability to properly metabolize glucose causes metabolic disturbances that eventually damage the eyes, kidneys, heart and other organs. Taking insulin parenteral^ can partially control these metabolic problems. Type 1 DM results from an autoimmune attack on the pancreatic beta cells, which are the source of insulin. Activated macrophages and cytotoxic T cells surround and destroy the pancreatic beta cells. Genetic susceptibility and poorly defined environmental events trigger the disease process.

D. Lupus Erythematosus (LE):

LE is a systemic autoimmune disease that is most frequent in women of early to middle adulthood. The tissue damage is caused by autoantibodies and hyperreactive regulatory T cells. The abnormal immune response allows sustained production of pathogenic autoantibodies and immune complexes, probably related to hypersensitivity type III. This leads to damage of the musculoskeletal, cutaneous, hematologic, renal tissues and other tissue systems. The abnormal immune response probably depends upon the interaction of multiple hereditary and environmental factors.

E. Sarcoidosis:

Sarcoidosis is a chronic granulomatous disease of the lungs and other organs of unknown cause. Most patients present between the ages of 20-40. The most frequent symptom is shortness of breath. The disease results from an exaggerated Th1-type, cellular immune response, probably to a limited number of antigens. Sarcoidosis develops throughout the world and afflicts all races. However, there is remarkable diversity of the prevalence of sarcoidosis among certain ethnic and racial groups. For instance, the disease is rare in Poland, Southeast Asia and India.

F. Multiple Sclerosis (MS):

MS is a chronic relapsing, multifocal inflammatory disorder of the central nervous system that leads to focal demyelination and scarring of the brain. It is a frequent disease affecting about 1 mio people in the western world and which often begins during early to middle adulthood. MS is an autoimmune disease mediated at least in part by Th1 cells. The lesions of MS resemble those induced by delayed hypersensitivity responses that contain activated T cells and macrophages. It is a disease of temperate climates, increasing in prevalence with distance from the equator.

G. Psoriasis

Psoriasis is a chronic relapsing dermatitis, which may be found in 2-3% of the populations in the Western communities. The disease is typically diagnosed for the first time in 10 to 30 y old individuals and is associated with aberrant immune responses. The abnormal immune response probably depends upon multiple hereditary and poorly defined environmental factors.

H. Autism

Autism is characterised by behavioural and developmental deviations resulting in poor social performance. Autism may be found in up to 1% of the population; however, the incidence is steadily increasing. The aetiology is unknown, but there is a strong genetic component, and the disease is particularly common in families with predisposition for autoimmune disorders, and therefore autoimmunity may be involved.

I. Allergy

As for classical auto-immune diseases (such as diseases mentioned above), the relevance of helminth infection to modify hyper-reactive immune responses in allergic disease phenotypes (e.g. type I hypersensitivity diseases like atopy, food allergy, asthma, allergic rhinitis, and atopic dermatitis) should be seen in the context of the hygiene hypothesis. The incidences of these diseases are increasing steadily in the industrialized world with a high level of hygiene and sanitation. Observational studies on microbial exposures have most consistently reported that particularly helminth infection is associated with a reduced risk of atopy and allergic disease. Generally, helminth infection presents with a high level of IgE antibody in serum otherwise only seen in allergic disease. However, in allergic individuals, IgE against e.g. pollen triggers allergic inflammation due to mast cell activation and degranulation with associated immediate symptoms (e.g. swellings, sneezing and lacrymation), while helminth infection is often asymptomatic due to a state of hyporesponsiveness to the helminths. Infection with different species of helminth (e.g. schistosomes and hookworm) has been associated with reduced risk of atopy, suggesting a common biological mechanism. The state of hyporesponsiveness during helminth infection presents immunological characteristics, which are similar to those observed during effective allergen immune therapy for allergic rhinitis, including production of the cytokine IL-10, and specific IgG4 to antigens/allergens. Both allergic reactions and helminth infection are characterised by a so-called Th2 cytokine profile (IL-4, IL-5, and IL-13). However, during chronic helminth infection this profiles is modified by the cytokines IL-10 and TGFβ believed to have anti-inflammatory regulatory properties. Murine models of helminth infection and allergic diseases support the above observations in humans.

Observational studies have mostly focused on the relationship between asthma and helminths, and these studies further suggests that the observed reduction in risk of asthma might be stronger for infection with helminth species with a systemic phase in their human host, and/or to be strengthened with increasing intensity of infection measured by number of eggs in faeces. Currently, it is believed that helminths or their excretory products carry signature molecules that are particular suitable for the natural induction of a robust anti-inflammatory regulatory network that could prevent or alleviate symptoms of allergic disease. Evidence for a direct cause-effect relationship between helminth infection and reduced risk of allergic disease has been suggested by studies showing that anti-worm treatment in endemic areas effectively removes high worm burdens but such treatment is temporally associated with an increase in positive skin reactions to allergens (atopy).

The occurrence of above mentioned disease complexes (A-G) have to a variable degree been described in domestic animals, although background and clinical manifestation may be different from the equivalent disease in humans. However, there is strong reason to believe that these diseases in animals are also treatable relevant to the invention. Evidence of the above-mentioned autoimmune and allergic diseases as well as cure or amelioration thereof is required to determine the need for treatment and to monitor treatment progress. The following procedures can be utilized to measure the clinical parameters of the above-mentioned diseases in man.

1. Inflammatory Bowel Disease (IBD)

Evaluation of inflammation: In mice, clinical evidence of disease includes weight loss, diarrhoea, rectal prolapse and histological evidence of intestinal inflammation. Thus, improvement in these parameters would signify amelioration of disease.

To grade intestinal inflammation in animal models, tissue is removed, Swiss-rolled and embedded in paraffin according to standard methods. The sections are stained with hematoxylin and eosin. The degree of colonic inflammation is graded semi-quantitatively from 0 to 4 in a blinded fashion by a single pathologist using a standardized technique: 0=no inflammation; 1=low level inflammation; 2=intermediate level inflammation; 3=high level inflammation with wall thickening; and 4=transmural infiltration, and loss of goblet cells with wall thickening.

To count mast cells, intestinal tissue samples from individual mice are prepared by the Swiss-roll technique, fixed in Carnoy's fixative, paraffin embedded and processed for staining with Alcian Blue and safranin. Fifty adjacent fields of a given section are scanned for mucosal mast cells in the lamina propria and muscle layers. Mast cells are identified by their distinctive intracellular granular staining with Alcian Blue. All samples are evaluated blindly.

Disease activity in humans is monitored using various clinical, laboratory and histological criteria. There are several well established IBD disease activity indices that monitor clinical parameters like frequency of diarrhoea and abdominal pain. One particularly useful index for the assessment of Crohn's disease is the Crohn's Disease Activity Index, or CDAI. The CDAI incorporates 8 variables related to the disease activity and has been used in most recent studies of therapeutic agents in Crohn's disease. It includes the number of liquid or very soft stools, the severity of abdominal pain or cramping, general well-being, the presence of extra-intestinal manifestations of the disease, presence or absence of an abdominal mass, use of antidiarrhoeal drugs, hematocrit, and body weight. The composite score ranges from 0 to about 600. Scores below 150 indicate remission and scores above 450 indicate severe illness.

A tested, accepted and disease specific quality of life questionnaire also may be administered prior to and after treatment to assess therapeutic progress. The Irvine Inflammatory Bowel Disease Questionnaire is a 32-item questionnaire. It evaluates quality of life with respect to bowel function (e.g. loose stools and abdominal pain), systemic symptoms (fatigue and altered sleep pattern), social function (work attendance and the need to cancel social events) and emotional status (angry, depressed, or irritable). The score ranges from 32 to 224, with higher scores indicating a better quality of life. Patients in remission usually score between 170 and 190.

Also, helpful are endoscopic, x-ray and histological assessment of intestinal disease activity. C-reactive protein levels and blood cell sedimentation rate may also be monitored as systemic indicators of inflammation.

2. Rheumatoid Arthritis

Evaluation of inflammation: For mice with collagen-induced arthritis, mice are examined every other day and their paws scored as follows: 0, normal; 1, Erythema and mild swelling confined to the ankle joint or toes; 2, Erythema and mild swelling extending from the ankle to the midfoot; 3, Erythema and severe swelling extending from the ankle to the metatarsal joints; and 4, Ankylosing deformation with joint swelling. These arthritis scores can be correlated with the histological changes in the arthritic joints. Treatment success results in a decrease in the arthritis score with improvement in the histology.

For pristane-induced arthritis, joints may be measured with a micrometer to detect swelling. In humans, RA is scored by measuring joint swelling, erythema, limitation of motion and pain. Additionally, synovial fluid may be analyzed for cytokine and inflammatory protein concentrations, and for leukocyte composition and function, according to methods known in the art. Synovial biopsies provide tissue for histological analysis according to methods known in the art.

3. Lupus Erythematosus

Evaluation of inflammation: The normal development and function of the immune system critically depends on the removal of unwanted cells by a process called apoptosis. Cell-to-cell interactions through specific cell surface molecules and their receptors frequently trigger the process. One such system is called FAS and FAS ligand. Mice deficient in either FAS (LPR-1-mice) or FAS ligand (GLD-1-mice) develop an autoimmune disease like lupus.

Colonies of LPR or GLD mice are maintained in microisolator housing units under specific pathogen-free conditions. These mice can develop autoimmunity spontaneously, but more predictably after artificial induction. To induce disease, 8-wk-old mice are injected with an agent like pristane. Within two months, the mice have autoimmune disease. Many clinical, histological and immunological criteria useful for judging disease induction and amelioration in both mice and humans are well known in the art.

4. Juvenile Insulin-Dependent Diabetes Mellitus (Type 1)

Evaluation of inflammation: The NOD mouse develops type 1 diabetes mellitus similar to humans due to autoimmune destruction of the pancreatic beta cells. Clinical, biochemical, immunological and histological examination according to methods known in the art allow assessment of disease induction and amelioration in mice.

5. Sarcoidosis

Evaluation of inflammation: In the bead embolization model of pulmonary inflammation, antigens are coupled to Sepharose beads, which are embolized to the lungs of mice via injection into their tail veins. The animals usually are pre-sensitized to the coupled antigen. The immune system of the host mounts a vigorous immune response to the offending bead. These focal inflammatory responses, which can last for several weeks, can be examined histologically for size. Also, they can be isolated from tissue and studied for cell composition and cytokine production. Moreover, hilar lymph nodes and spleens are readily available for experimentation. Sarcoidosis, a disease of humans, usually involves the lung. Determination of sarcoidosis and the extent of the disease may be made according to methods known in the art. Pulmonary function tests can assess lung compliance and function. Also, bronchiolar lavage obtains inflammatory cells that have infiltrated into the bronchial tree during the inflammatory process. These cells can be studied for composition and function. Pulmonary infiltrates and hilar lymphadenopathy are characteristic of sarcoidosis. Thus, periodic chest x-ray or CT scans can help assess disease activity. Serologic tests, such as measurement of angiotensin converting enzyme activity according to methods known in the art, can be used to gauge disease extent and activity.

6. Multiple Sclerosis

Evaluation of inflammation: Experimental autoimmune encephalomyelitis is induced in susceptible mice by repeated injection of appropriate sensitizing myelin antigens. Mice are assessed clinically according to the following criteria: 0, no disease; 1, tail atony; 2, hind-limb weakness; 3, hind-limb paralysis; 4, hind-limb paralysis and forelimb paralysis or weakness; 5, moribund. For histological analysis, the spinal cords and brains are removed and fixed in formalin. The paraffin-embedded sections are stained and examined under light microscopy. Dispersed splenocytes and cells from other regions can be studied in-vitro. These parameters can help measure disease amelioration or improvement.

In humans, MS disease activity is gauged by monitoring progression and remittance of neurological signs and symptoms. The most widely used outcome measurement is called The Expanded Disability Status Scale. Cerebral spinal fluid protein composition and cell content analyzed according to methods known in the art also may be used to monitor disease activity. Moreover, serial MRI studies show new gadolinium-enhanced brain lesions.

7. Psoriasis

Psoriasis may be measured simply by estimating the percentage of the skin that is affected with dermatitis or more adequately by the PASI (Psoriasis Activity and Severity Index) score that reflects the intensity of the skin lesions over time in combination with the size of the affected skin area.

8. Autism

Autism is a behavioral disorder and the severity of the symptoms can only be scored by behavioral studies.

9. Allergy

Allergy is a complex of diseases associated with immediate symptoms as swellings, sneezing and lacrymation, and the scoring of diseases is among others done through measure of the severity of the specific symptoms related to exposure to the relevant allergen.

Compositions According to the Invention

According to a first aspect of the present invention there is provided a composition for storage of eggs from helminthic parasites, such as the pig whipworm *Trichuris suis*, said composition further comprising a liquid carrier having a pH value of below 7 at a temperature of from 0° C. to 30° C. or from 5° C. to ambient temperature.

The liquid carrier can be sulphuric acid, $H_2SO_4$, such as H2SO4 having a pH below 6, such as H2SO4 having a pH of 0-6, such as $H_2SO_4$ having a pH of 0-5, such as $H_2SO_4$ having a pH of 0-1; such as $H_2SO_4$ having a pH of 1-2; such as $H_2SO_4$ having a pH of 2-3; such as $H_2SO_4$ having a pH of 3-4; such as $H_2SO_4$ having a pH of 4-5; such as $H_2SO_4$ having a pH of 5-6. A pH of from 0 to 2 is preferred. Other acidic liquid carriers and addition of antibiotics can also be used.

According to one or more embodiments of the first aspect of the invention, the helminthic parasite may be selected from nematode genera such as *Ascaris, Enterobius, Trichuris, Ancylostoma, Necator*, and *Strongyloides*. The first aspect of the invention also covers an embodiment, wherein the helminthic parasite is a platyhelminth. It is also within an embodiment of the first aspect of the invention that the helminthic parasite may be selected from the group consisting of trematodes and cestodes. It is within one or more embodiments of the first aspect of the invention that the helminthic parasite is selected from the parasite genera *Fasciolopsis, Echinostoma, Heterophyes, Clonorchis, Opisthorchis, Fasciola, Schistosoma, Diphyllobothrium, Taenia* and *Hymenolepsis*.

It is also within an embodiment of the first aspect of the invention that the helminthic parasite is selected from the group consisting of filarial parasites and lung flukes.

Furthermore, the first aspect of the invention covers embodiment(s), wherein the helminthic parasite is selected from the group consisting of genera *Trichuris, Nippostrongylus, Heligmosomoides, Hymenolepsis, Angiostrongylus, Ascaris, Toxocara, Gnathostoma, Ancylostoma, Anisakis* and *Pseudoterranova*.

In a preferred embodiment of the first aspect of the invention the helminthic parasite is *Trichuris suis*. Here, the composition may be obtained by a method comprising the steps of infecting an animal, such as a pig, with *T. suis*, isolating the eggs in the animal faeces after a suitable time, such as e.g. after about 5 to 30 weeks or after about 5-11 weeks, such as after about 7 to 9 weeks after inoculation, and adding to the isolated eggs a liquid carrier having a pH value of below 7 at a temperature range of from 0° C. to 30° C. or from 5° C. to ambient temperature. It is preferred that the isolation step comprises a washing procedure employing a series of washing steps using certified sieves (such as for example 1000, 500, 250, 100, 80, 70, 60, 50, and 20 μm mesh sizes) of large diameter (e.g. Ø450 mm), wherein the repeated washing steps employs sieves having a decreased mesh size, thereby allowing the eggs to be efficiently washed and separated from e.g. undigested plant material in the faeces material. It is preferred that the parasite eggs are contained in the sieved fraction and have a particle size of from 20-50 μm.

When the helminthic eggs are of the species *Trichuris suis* (TSO), the first aspect of the invention also covers an embodiment, wherein the composition is obtained by a method comprising the step of recovering parasite eggs from worms isolated directly from the intestine of pigs or from intestinal contents, and adding said eggs to a liquid carrier having a pH value of below 7 at a temperature range of from 0° C. to 30° C. Here, the isolated worms may be washed once or more than once in a medium optionally comprising one or more antibiotics prior to the recovery of the eggs. It is preferred that the isolated worms are retained in vitro in growth medium, optionally supplemented with antibiotics, wherein the isolated worms lay their eggs. The eggs may be separated from the growth medium by filtration on a sieve (e.g. 50 μm) prior to being added to said liquid carrier.

Methods According to the Invention

According to a second aspect of the present invention there is provided a method for the isolation and storage of eggs from the pig whipworm *Trichuris suis*. The method of the second aspect of the invention comprises the steps of a) isolation of parasite eggs either 1) in vitro, where worms removed for the intestine of pigs lay their eggs in a suitable media, or 2) from fecal material of the pigs, whereto the eggs are shed by the worms found in the intestine, and b) storage of the isolated and optionally cleaned eggs in an acidic medium, such as e.g. $H_2SO_4$, such as $H_2SO_4$ having a pH of 0-2 or 0-1 or 1-2, to allow for the development of the eggs (embryonation) and to inactivate any contaminating bacteria and viruses.

According to a third aspect of the present invention there is provided a method for the isolation and storage of eggs from the pig whipworm *Trichuris suis*, said method comprising the steps of a) isolating parasite eggs either 1) in vitro, where worms removed for the intestine of pigs lay their eggs in a suitable media, or 2) from fecal material of the pigs, whereto the eggs are shed by the worms found in the intestine, b) filtering the isolated material to reduce particle contamination and eggs of foreign pig parasites, c) floating the isolated material to reduce particle contamination, d) washing the isolated material in an acidic medium, such as e.g. sulphuric acid, $H_2SO_4$, such as $H_2SO_4$ having a pH of 0-2 or 0-1 or 1-2, to reduce the counts of foreign pathogens (bacteria, fungi and viruses) both by dilution and inactivation, e) storage of the isolated and cleaned eggs in an acidic medium, such as e.g.

$H_2SO_4$, such as $H_2SO_4$ having a pH of 0-2 or 0-1 or 1-2, to allow for the development of the eggs (embryonation) and to further inactivate and prevent growth of bacteria, fungi and viruses, f) filtering and floating the embryonated eggs to isolate the fraction of eggs that have the highest degree of embryonation (biotic potential of the pharmaceutical raw material), and g) storing the isolated and embryonated eggs in an acidic medium, such as e.g. $H_2SO_4$, such as $H_2SO_4$ having a pH of 0-2 or 0-1 or 1-2, that allows for maintenance of the biotic potential and the prevention of pathogen growth.

For the methods of both the second and third aspect of the invention it is preferred that the acidic medium used for storage of the eggs is a liquid carrier having a pH value of below 7. The liquid carrier can be sulphuric acid, $H_2SO_4$, such as $H_2SO_4$ having a pH below 6, such as $H_2SO_4$ having a pH of 0-6, such as $H_2SO_4$ having a pH of 0-5, such as $H_2SO_4$ having a pH of 0-1; such as $H_2SO_4$ having a pH of 1-2; such as $H_2SO_4$ having a pH of 2-3; such as $H_2SO_4$ having a pH of 3-4; such as $H_2SO_4$ having a pH of 4-5; such as $H_2SO_4$ having a pH of 5-6. A pH of from 0 to 2 or is preferred. Other acidic liquid carriers and addition of antibiotics can also be used.

For the methods of both the second and third aspect of the invention, these methods also cover embodiments further comprising a step, wherein the eggs stored in the acidic medium are developed from un-embryonated eggs (containing undifferentiated cells) into fully embryonated eggs (containing infective larvae stages), to thereby obtain a suspension of embryonated eggs in the acidic medium. When the acidic medium comprising the embryonated egg is $H_2SO_4$ having a pH in the range of 0-2, then this will allow for oral administration of the suspension. For the method of the third aspect of the invention, then according to one embodiment step b) is optional. It is also within an embodiment of the third aspect of the invention that step c) is optional. The third aspect of the invention also covers embodiments wherein step d) is optional and/or wherein step f) is optional.

According to a fourth aspect of the invention there is provided a method for producing a pharmaceutical composition comprising a helminthic parasite preparation, comprising the steps of:

(1) raising a preparatory animal in a specific human pathogen-free environment;

(2) obtaining a first helminthic parasite isolate from said preparatory animal;

(3) extracting eggs from said first helminthic parasite isolate, in vitro or from faecal cultures;

(4) storing un-embryonated eggs from said first helminthic parasite isolate in a composition further comprising an acidic liquid carrier; and (5) embryonating eggs from said helminthic parasite isolate under suitable conditions in said acidic liquid carrier to generate a pharmaceutical composition.

It is within an embodiment of the fourth aspect of the invention that the method further comprises the step of: (6) storing the embryonated eggs from said helminthic parasite isolate under suitable conditions in the acidic liquid carrier.

Also for the fourth aspect of the invention it is preferred that the acidic liquid carrier has a pH value of below 7. The liquid carrier can be sulphuric acid, $H_2SO_4$, such as $H_2SO_4$ having a pH below 6, such as $H_2SO_4$ having a pH of 0-6, such as $H_2SO_4$ having a pH of 0-5, such as $H_2SO_4$ having a pH of 0-1; such as $H_2SO_4$ having a pH of 1-2; such as $H_2SO_4$ having a pH of 2-3; such as $H_2SO_4$ having a pH of 3-4; such as $H_2SO_4$ having a pH of 4-5; such as $H_2SO_4$ having a pH of 5-6. A pH of from 0 to 2 is preferred. Other acidic liquid carriers and addition of antibiotics can also be used. It is within an embodiment of the fourth aspect of the invention that the step of isolating a helminthic parasite comprises obtaining stool from said preparatory animal, and isolating the helminthic parasite from said stool. Here, the step of isolating a helminthic parasite may comprise removing tissue from said preparatory animal, and isolating the helminthic parasite or its eggs from said tissue. Preferably, the tissue may be an internal organ such as intestines. It is also preferred that the step of isolating said helminthic parasite further comprises the steps of:

(1) dissecting the tissue from said preparatory animal to allow for macroscopical isolation of worms to produce a worm culture wherein the worms lay eggs, (2) filtering the worm culture to produce a filtrate with eggs; and (3) isolating the eggs from said filtrate, thereby extracting eggs from said helminthic parasite isolate.

According to an embodiment of the fourth aspect of the invention, the helminthic parasite preparation may comprise a parasite, which is a nematode.

The fourth aspect of the invention also covers one or more embodiments, wherein the helminthic parasite preparation comprises a parasite selected from the group consisting of the genera *Ascaris, Enterobius, Trichuris, Ancylostoma, Necator, Strongyloides*.

It is also within an embodiment of the fourth aspect of the invention that the helminthic parasite preparation comprises a parasite which is a platyhelminth. It is also within an embodiment of the fourth aspect of the invention that the helminthic parasite preparation comprises a parasite selected from the group consisting of trematodes and cestodes.

It is within one or more embodiments of the fourth aspect of the invention that the helminthic parasite preparation comprises a parasite selected from the group consisting of genera *Fasciolopsis, Echinostoma, Heterophyes, Clonorchis,*

*Opisthorchis, Fasciola, Schistosoma, Diphyllobothrium, Taenia* and *Hymenolepsis*. It is also within an embodiment of the fourth aspect of the invention that the helminthic parasite preparation comprises a parasite selected from the group consisting of filarial parasites and lung flukes.

Furthermore, the fourth aspect of the invention covers embodiment(s), wherein the helminthic parasite preparation comprises a parasite selected from the group consisting of genera *Trichuris, Nippostrongylus, Heligmosomoides, Hymenolepsis, Angiostrongylus, Ascaris, Toxocara, Gnathostoma, Ancylostoma, Anisakis* and *Pseudoterranova*.

In a preferred embodiment of the fourth aspect of the invention, the helminthic parasite is *Trichuris suis*.

According to a fifth aspect of the present invention, there is provided a method for prophylactic, ameliorating or curative treatment of an autoimmune or allergic disease in an individual man or animal, said method comprising the steps of providing a composition according to an embodiment selected from any of the embodiments of the first aspect of the invention, isolating helminthic worms from the intestines, incubating the isolated worms under suitable growth conditions under which they will lay eggs, separating the eggs from the media or isolating the eggs from intestinal contents, transfer the eggs to an acidic liquid carrier thereby obtaining a suspension of helminthic eggs, mixing the eggs with a pharmaceutically acceptable carrier to generate a pharmaceutical composition and administering said pharmaceutical composition in a pharmaceutically effective amount to an individual, man or animal, suffering from an autoimmune or allergic disease, or to prevent the occurrence of such diseases.

According to a sixth aspect of the present invention, there is provided a method for treating an autoimmune or allergic disease in an individual man or animal, said method comprising the steps of providing a composition according to an embodiment selected from any of the embodiments of the first aspect of the invention, embryonating eggs from the helminthic parasite under suitable conditions in the acidic liquid carrier, thereby obtaining a pharmaceutical composition and administering said pharmaceutical composition in a pharmaceutically effective amount to an individual man or animal suffering from an autoimmune or allergic disease or to prevent the occurrence of such disease.

According to an embodiment of the fifth or sixth aspect of the invention the autoimmune disease may be inflammatory bowel disease. The inflammatory bowel disease may be Crohn's disease (CD) or Ulcerative colitis (UC).

It is also within an embodiment of the fifth or sixth aspect of the invention that the autoimmune disease may be rheumatoid arthritis.

According to an embodiment of the fifth or sixth aspect of the invention the autoimmune disease may be lupus erythematosus.

It is also within an embodiment of the fifth or sixth aspect of the invention that the autoimmune disease may be type 1 diabetes mellitus.

It is also within an embodiment of the fifth or sixth aspect of the invention that the autoimmune disease may be sarcoidosis. The fifth or sixth aspect of the invention also covers an embodiment wherein the autoimmune disease is multiple sclerosis.

It is also within an embodiment of the fifth or sixth aspect of the invention that the autoimmune disease may be psoriasis, or the autoimmune disease may be autism.

According to an embodiment of the fifth or sixth aspect of the invention the disease may be allergy.

According to a seventh aspect of the present invention there is provided a method of treating an excessive immune response in an individual man or animal, said method comprising the steps of providing a composition according to an embodiment selected from any of the embodiments of the first aspect of the invention, embryonating eggs from the helminthic parasite under suitable conditions in the acidic liquid carrier, thereby obtaining a pharmaceutical composition and administering said pharmaceutical composition in an amount sufficient to reduce the excessive immune response in the individual, man or animal. Here, the excessive immune response may be an enhanced Th1 immune response. According to an eight aspect of the present invention there is provided a method for prolonging organ allograft survival in an individual, man or animal, said method comprising down-regulating the Th1 immune activity in the individual man or animal by administering to the individual an effective Th2 up-regulating amount of a pharmaceutical composition comprising a Th2 up-regulating activity, said method comprising the steps of providing a composition according to an embodiment selected from any of the embodiments of the first aspect of the invention, embryonating eggs from the helminthic parasite under suitable conditions in the acidic liquid carrier, thereby obtaining a pharmaceutical composition comprising a Th2 up-regulating activity and administering said pharmaceutical composition in an amount sufficient to prolong organ allograft survival in the individual man or animal by down-regulating the Th1 activity in the individual.

It is also within an embodiment of the eight aspect of the invention, said treatment may be ameliorating, prophylactic or curative.

It is within an embodiment of the fifth, sixth, seventh or eight aspect of the invention that the individual is a mammal, such as a human or a domestic animal.

According to a ninth aspect of the present invention there is provided a use of a composition according to an embodiment selected from any of the embodiments of the first aspect of the invention in the manufacture of a medicament or a pharmaceutical composition for treating an autoimmune or allergic disease in an individual man or animal in need of said treatment. Here, the autoimmune disease may be inflammatory bowel disease. The inflammatory bowel disease may be Crohn's disease (CD) or Ulcerative colitis (UC).

According to an embodiment of the ninth aspect of the invention, the autoimmune disease may be rheumatoid arthritis.

The ninth aspect of the invention also covers an embodiment, wherein the autoimmune disease is lupus erythematosus. It is also within an embodiment of the ninth aspect of the invention that the autoimmune disease may be type 1 diabetes mellitus. Furthermore, the ninth aspect of the invention covers an embodiment, wherein the autoimmune disease is sarcoidosis, and an embodiment, wherein the autoimmune disease is multiple sclerosis.

It is also within an embodiment of the ninth aspect of the invention that the autoimmune disease may be psoriasis or that the autoimmune disease may by autism.

According to an embodiment of the ninth aspect of the invention the autoimmune disease may be allergy.

It is also within an embodiment of the ninth aspect of the invention that the manufacture of the medicament comprises a method selected of any of the embodiments of the fourth aspect of the invention.

According to a tenth aspect of the present invention there is provided a use of a composition according to an embodiment selected from any of the embodiments of the first aspect of the invention in the manufacture of a medicament or a pharmaceutical composition for treating an excessive immune response in an individual man or animal in need of said treatment. Here, the excessive immune response may be an enhanced Th1 response.

It is within an embodiment of the ninth or tenth aspect of the invention that said treatment is ameliorating, prophylactic or curative. It is also within an embodiment of the ninth or tenth aspect of the invention that the individual is a mammal, such as a human or a domestic animal.

Further features and advantages of the invention will become more fully apparent with reference to the following drawings and description of preferred embodiments.

BRIEF DESCRIPTION OF THE ILLUSTRATIONS

Figure 2:
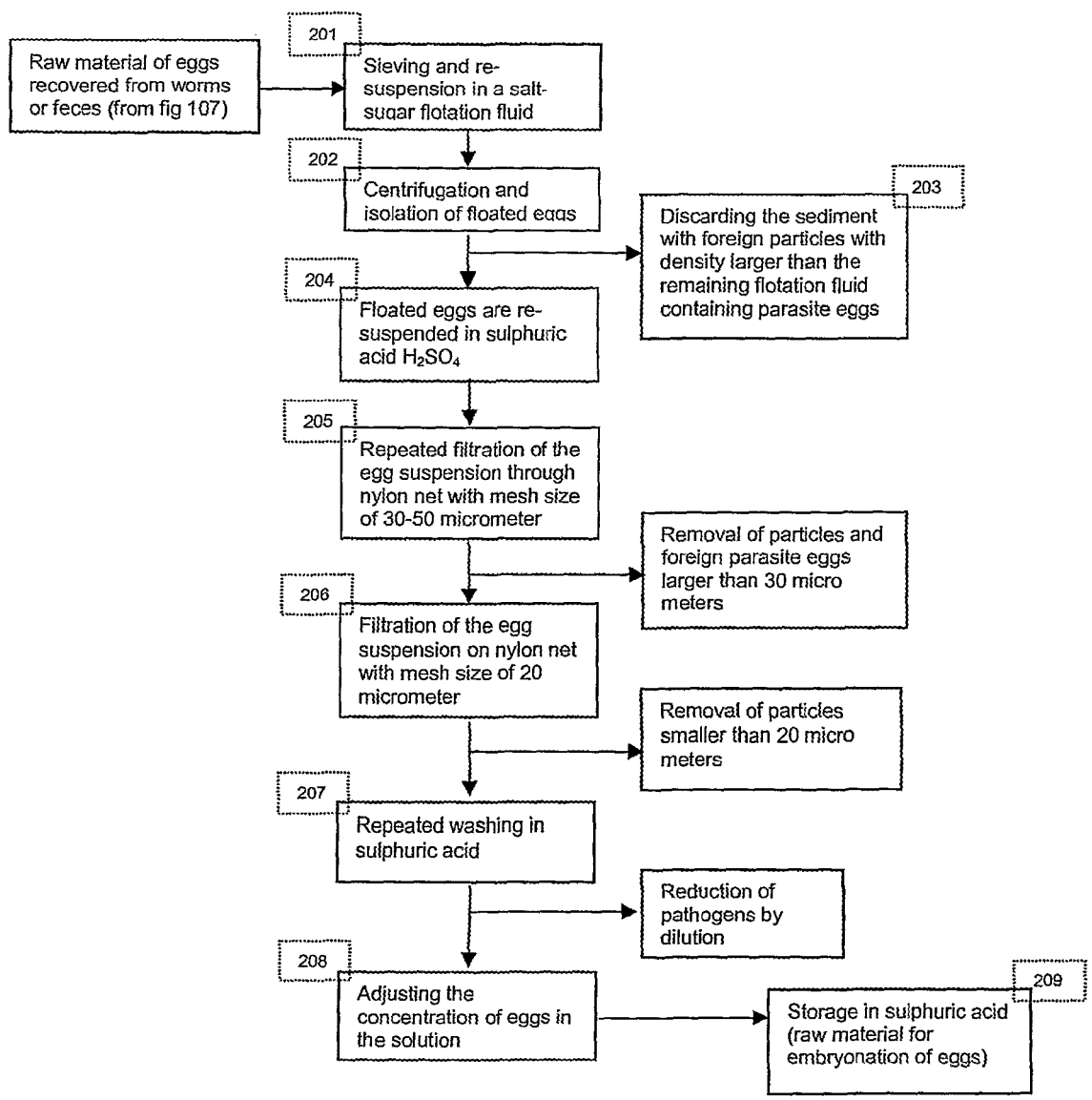
Figure 3:
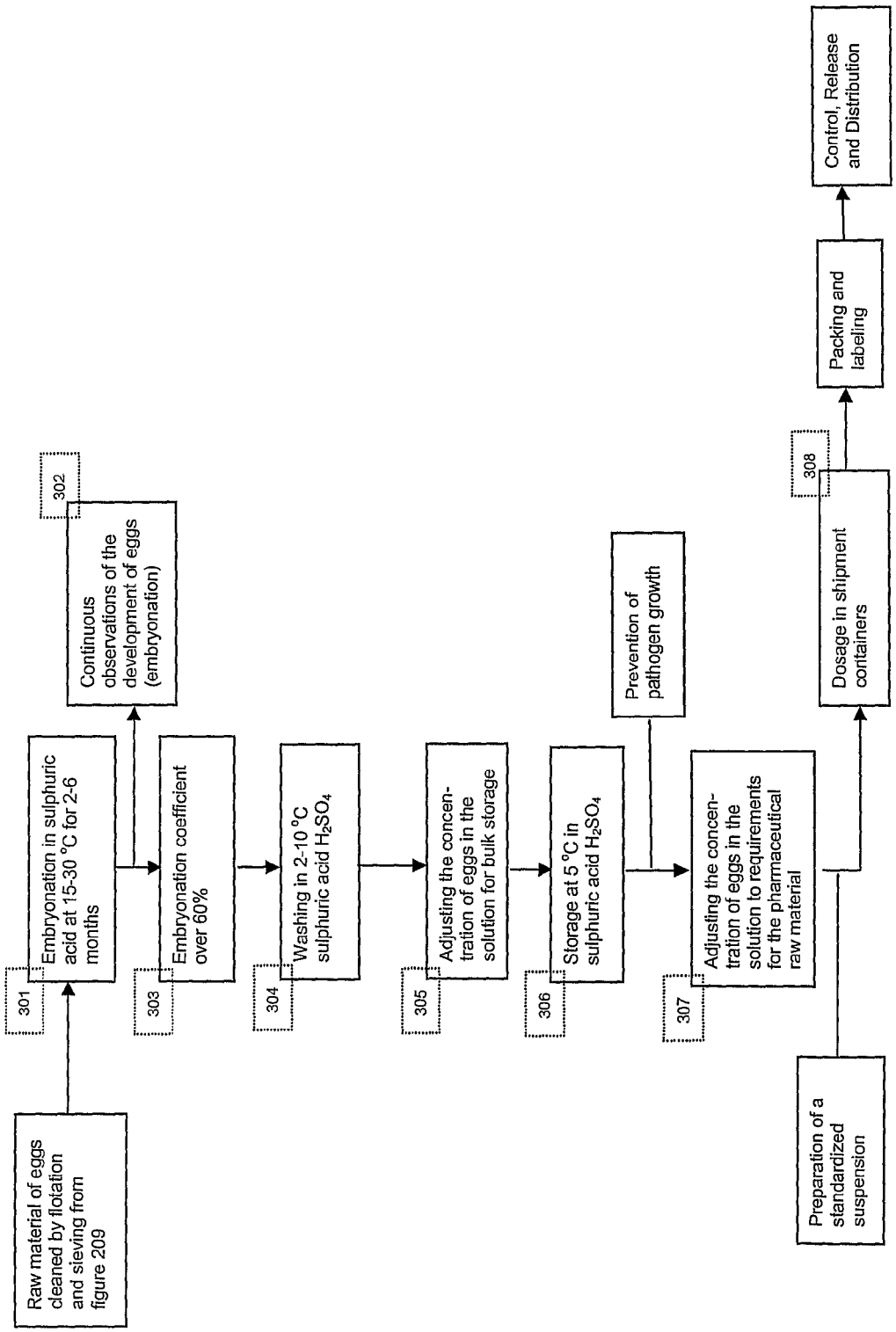
Figure 4:
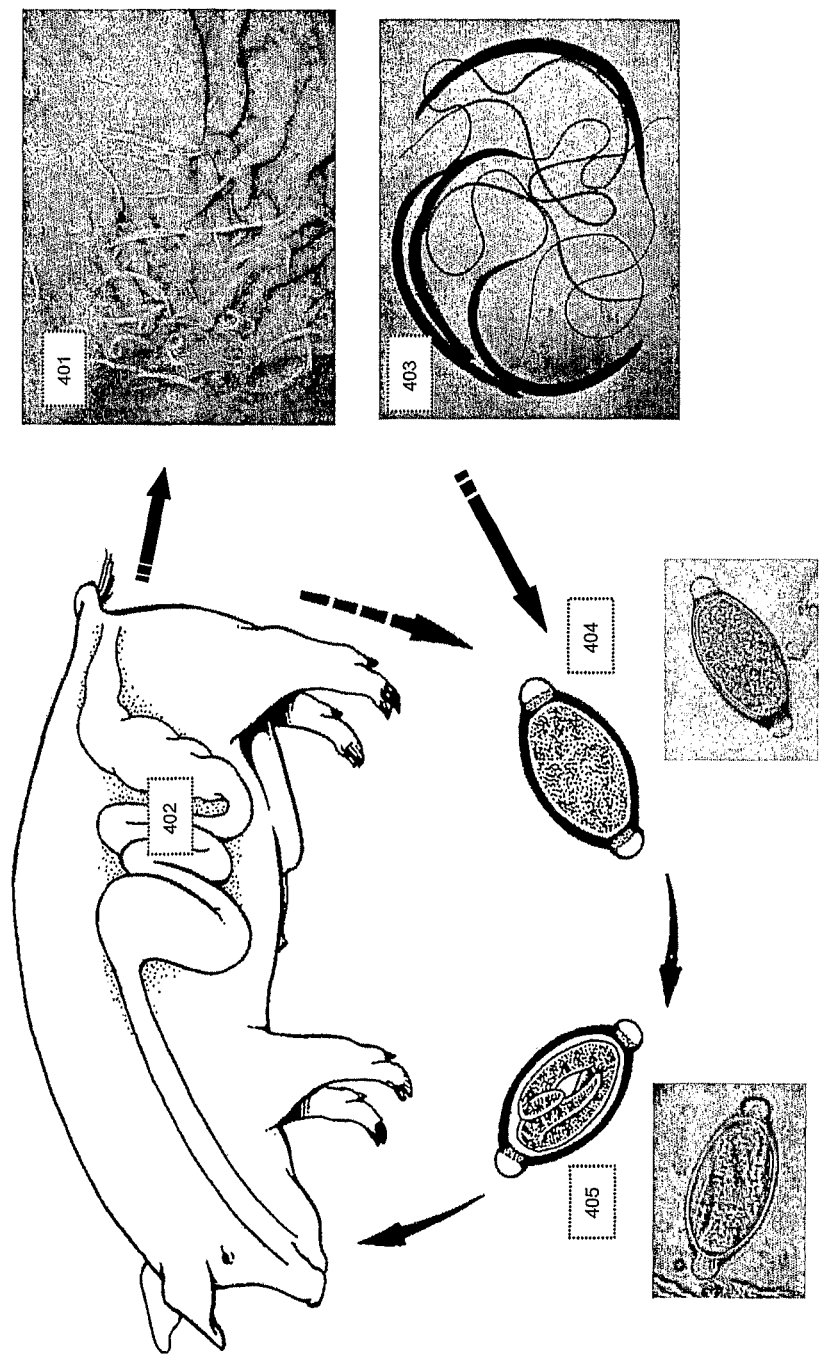

FIG. 1 is a flow chart illustrating a method for the isolation of parasite eggs from faeces (deposited by intestinal worms in situ) or from worms in culture (deposited by isolated worms in vitro) of pigs infected with the whipworm, Trichuris suis according to an embodiment of the present invention, FIG. 2 is a flow chart illustrating a method for reduction of particle contamination and removal of foreign parasite eggs in a suspension of eggs of the pig whipworm Trichuris suis according to an embodiment of the present invention, FIG. 3 is a flow chart illustrating a method for embryonation, storage and preservation of eggs of the pig whipworm Trichuris suis to be used as a raw material for a pharmaceutical agent for oral administration according to an embodiment of the present invention, and FIG. 4 illustrates the lifecycle of the pig whipworm Trichuris suis.

DETAILED DESCRIPTION OF THE INVENTION

In the following (steps 1-9) is given a detailed description of embodiments relating to the present invention. The embodiments cover recovery of parasite eggs (1, 2), reduction of particle contamination (3, 4), removal of foreign parasite eggs (5), washing in an acidic medium (6), embryonation of parasite eggs (7), storage of parasite eggs (8), and administration of a parasite egg suspension (9).

1. Recovery of Parasite Eggs from Faeces (Worms In Situ)

Pigs infected with the common intestinal worm T. suis will excrete parasite eggs to the faeces of the pigs approximately 7-9 weeks after they are inoculated. These eggs may be collected in high quantities from the faeces. The isolation process relies on washing procedure on series of certified steel sieves (for example 1000, 500, 250, 100, 80, 70, 60, 50, and 20 µm mesh sizes) of large diameter (e.g. Ø450 mm). The repeated washing procedure on sieves with decreasing mesh size, allows the eggs to be efficiently washed off the undigested plant fibres in the faeces material. The parasite eggs are contained in the sieved fraction with particle size 20-50 µm. The 20-50 µm fraction is re-suspended in $H_2SO_4$ (e.g. pH 0-2), eventually added antibiotics, to minimize pathogen growth and is further processed in steps 3 and/or 4 below.

2. Recovery of Parasite Eggs from Worms (Worms In Vitro)

Eggs may alternative be recovered in lower numbers from worms that are isolated directly from the intestine of pigs. After repeated washes in media with antibiotics, the worms are kept in vitro in growth media with antibiotics or other preservatives wherein they lay their eggs. The eggs are separated from the media by filtration on a 50 µm sieve followed by filtration on a 20 µm sieve. The resulting 20-50 µm fraction is further processed in steps 3 and/or 4 below.

3. Reduction of Particle Contamination by Flotation

The egg suspensions originating from step 1 and/or step 2 constitute the initial material for a further reduction of contents of unwanted particles. In these suspensions, all particles are between 20 and 50 µm, but the eggs have lower density than most of the other particle (plant fibres and mineral particles). Therefore, the eggs may float in flotation fluids with specific gravidity of more than 1.18 g per ml, such as a saturated salt-sugar suspension, such as sodium chloride-glucose, or the eggs may float in solutions of magnesium sulphate or zinc chloride. By centrifugation, the eggs will float and the debris sediment. The floated eggs are isolated and washed on a 20 µm sieve and re-suspended in $H_2SO_4$ (e.g. pH 0-2).

4. Reduction of Particle Contamination by Filtration

The egg suspensions resulting from steps 1, 2 and/or 3, containing particles in the size range of 20-50 µm, is further cleaned by filtration at disposable nylon net with certified mesh size of 30-35 µm, recovering the eggs on 20-25 µm nylon net.

5. Removal of Foreign Parasite Eggs by Filtration

The filtration of the suspension at 30-35 µm ensures that the foreign parasite eggs, which may have been in the original faecal solution, are retained. Although Trichuris suis eggs are up to 80 µm in length they are only around 23-30 µm in width, slender and lemon-shaped and will orientate in the longitudinal direction of the current of the solution that passes a sieve. Thus, experiments have shown T. suis eggs will pass a 30 µm sieve. Other eggs with the potential to infect pigs will not: Ascaris suum (50-84 µm), Metastrongylus (38-64 µm) Strongyloides 30-57 µm, Globocephalus (40-72 µm), Oesophagostomum (38-83 µm), Hyostrongylus (31-76 µm), Macracanthorhynchus (65-110 µm). The eggs of a common round worm of cats and dogs Toxocara (75-90 µm) will also be retained.

6. Washing and Pathogen Inactivation by $H_2SO_4$ (e.g. pH 0-2)

Following the filtration, the suspension is washed repeatedly in $H_2SO_4$ (e.g. pH 0-2), to reduce any pathogen or pathogen spores by dilution. Further pathogen growth is prevented by $H_2SO_4$ (e.g. pH 0-2).

7. Embryonation of Trichuris suis Egg (TSO) in $H_2SO_4$ (e.g. pH 0-2)

The suspension is stored in an incubator at temperatures of 15-30° C. for development of the eggs from un-embryonated to embryonated. The process, embryonation will take from 2-6 months depending on incubation temperature.

8. Storage of Trichuris suis Eggs (TSO) in $H_2SO_4$ (e.g. pH 0-2)

After embryonation, the pharmaceutical raw material, can be stored at temperatures in the range of 1-10° C. with unchanged infectivity in periods up to several year. Thus, the larvae inside the egg will remain infective in this period. The acid will prevent pathogen growth.

9. Oral Administration of Egg Suspension (TSO) in $H_2SO_4$ (e.g. pH 0-2)

The suspension containing the embryonated helminthic eggs (with infective larvae) can be administered directly to an individual (man or animal) as an oral suspension either in capsules or by other means.

Methods and/or embodiments relating to the present invention are further described in the flow charts shown in FIGS. 1-3.

FIG. 1 is a flow chart illustrating methods for the isolation of parasite eggs from faeces (worms in situ) or intestinal worms (worms in vitro) of pigs infected with the whipworm *Trichuris suis* according to an embodiment of the present invention.

In FIG. 1 the starting point is inoculation of pigs with parasite material 101. Then in order to recover parasite eggs, two routes may be followed. The first route in FIG. 1 corresponds to step 2 outlined above and comprises the steps: Taking out the intestine 102a; harvesting the worms 103a; washing the worms 104a; in vitro recovery of eggs in the media used for cultivation of worms 105a; filtering and re-suspension of eggs in sulphuric acid ($H_2SO_4$) to minimize bacterial growth 106a; and ending up with raw material for reduction of particle contamination 107. The second route in FIG. 1 corresponds to step 1 discussed above and comprises the steps: Collecting fecal material 102b; suspending and sieving the fecal material 103b; recovery of a sieved fraction 104b; in vitro isolation of eggs from fecal material 105b; filtering and re-suspension of eggs in sulphuric acid ($H_2SO_4$) to minimize bacterial growth 106b; and ending up with raw material for reduction of particle contamination 107.

FIG. 2 is a flow chart illustrating a method for reduction of particle contamination and removal of foreign parasite eggs in a suspension of eggs of the pig whipworm *Trichuris suis* according to an embodiment of the present invention. The route described in the flowchart of FIG. 2 corresponds to steps 3-6 discussed above. The starting point is the raw material of eggs recovered from worms or feces following step 107 of FIG. 1. Then the method illustrated in FIG. 2 follows the steps: sieving and re-suspension of the eggs in a salt-sugar flotation fluid 201; centrifugation and isolation of floated eggs 202; discarding the sediment with foreign particles with density larger than the salt-sugar flotation fluid 203; re-suspending the floated eggs in sulphuric acid $H_2SO_4$ 204; filtration of the egg suspension through a nylon net with mesh size of 30-50 micrometer 205, followed by removal of particles and foreign parasite eggs larger than 30 micro meters; filtration of the egg suspension on nylon net with mesh size of 20 micrometer thereby removing particles smaller than 20 micrometers 206; repeated washing in sulphuric acid 207 to thereby reduce pathogens by dilution; adjusting the concentration of eggs in the solution 208; and storing the eggs in sulphuric acid 209 to thereby obtain raw material for embryonation of eggs.

FIG. 3 is a flow chart illustrating a method for embryonation, storage and preparation of eggs of the pig whipworm *Trichuris suis* to be used as a raw material for a pharmaceutical agent for oral administration according to an embodiment of the present invention. The route described in the flowchart of FIG. 3 corresponds to steps 7-9 discussed above. The starting point is the raw material of eggs cleaned by flotation and sieving step 209 of FIG. 2. Then the method illustrated in FIG. 3 follows the steps: embryonation of eggs in sulphuric acid at 15-30° C. for 2-6 months with repeated stirring or shaking 301 and continuous observations of the development from undifferentiated eggs into eggs containing larvae (embryonation) 302; the embryonation is allowed to progress until the embryonation coefficient is in the range of 60-90% or over 90% 303; washing of eggs in 2-10° C. sulphuric acid $H_2SO_4$ 304; adjusting the concentration of eggs in the solution for bulk storage 305; storage of eggs at 1-10° C. in sulphuric acid ($H_2SO_4$), eventually added antibiotics, to thereby prevent pathogen growth 306; adjusting the concentration of eggs in the solution to requirements for the pharmaceutical raw material 307, which may be followed by the preparation of a standardized suspension; a dose of the egg solution may be put into shipment containers 308, which may be followed by packing and labeling, control, release and distribution.

FIG. 4 illustrates the lifecycle of the pig whipworm *Trichuris suis*. Adult worms are found in and on the wall 401 of the large intestine of the pig 402. Eggs from the worm can be obtained in two ways: 1) either worms are transferred to a culture dish where they are incubated in a media 403 in which they lay their eggs, or 2) eggs are recovered directly from feces by sieving the fecal material. The resulting eggs from either 1) or 2) are un-embryonated 404 which contains undifferentiated material. After storage in acidic media for 2-6 months, eventually added antibiotics, eggs become embryonated 405 with a clearly visible larval structure inside. It is these embryonated eggs that constitute the active pharmaceutical agent for oral administration, *Trichuris suis* ova (TSO).

Other embodiments will be evident to those skilled in the art. It should be understood that the foregoing detailed description is provided for clarity only and is merely exemplary. The spirit and scope of the present invention are not limited to the above examples, but are encompassed by the following claims.

We claim:

1. A method for the isolation and storage of eggs from the pig whipworm *Trichuris suis*, said method comprising the steps of:
   a) isolating parasite eggs either using a method 1) comprising the steps of isolating eggs from worms which have been removed from the intestine of pigs and grown in a growth medium suitable for such growth, wherein the worms lay their eggs in said suitable growth medium, or a method 2) comprising the steps of using an infected pig, or infecting a pig, with *Trichuris suis* and isolating eggs from fecal material produced by said pig,
   b) washing repeatedly the isolated material in sulphuric acid $H_2SO_4$, having a pH of below 6, to reduce the counts of foreign pathogens both by dilution and inactivation, wherein the repeated washing steps comprises a series of repeated washing steps employing sieves having a decreased mesh size;
   c) storing the isolated eggs in sulfuric acid, $H_2SO_4$, having a pH of below 6 to inactivate any bacteria, fungi and/or viruses, if present,
   d) embryonating the *Trichuris suis* eggs by storing the composition of eggs and sulphuric acid in an incubator at temperatures of 15-30° C. in 2-6 months for development of the eggs from un-embryonated eggs to embryonated eggs, and
   e) storing the isolated and embryonated eggs at temperatures in the range of 1-10° C. in sulphuric acid, $H_2SO_4$ having a pH of below 6, thereby allowing for maintenance of biotic potential and the prevention of pathogen growth.

2. A method for producing a pharmaceutical composition comprising a *Trichuris suis* preparation, comprising the steps of:
   a) raising a preparatory animal in a specific human pathogen-free environment;
   b) obtaining a *Trichuris suis* isolate from said preparatory animal;
   c) extracting eggs from said *Trichuris suis* isolate;
   d) washing repeatedly the isolated material in sulphuric acid $H_2SO_4$, having a pH of below 6, to reduce the counts of foreign pathogens both by dilution and inactivation, wherein the repeated washing steps comprises a series of repeated washing steps employing sieves having a decreased mesh size;

e) storing un-embryonated eggs from said *Trichuris suis* isolate in a composition further comprising an acidic liquid carrier being sulphuric acid, $H_2SO_4$ having a pH of below 6;

f) embryonating eggs from said *Trichuris suis* isolate by storing the composition of eggs and sulphuric acid in an incubator at temperatures of 15-30° C. in 2-6 months for development of the eggs from un-embryonated eggs to embryonated eggs to generate a pharmaceutical composition; and g) storing embryonated eggs from *Trichuris suis* isolate at temperatures in the range of 1-10° C. in said acidic liquid carrier.

3. The method of claim 2, wherein the step of isolating *Trichuris suis* comprises obtaining a stool from said preparatory animal, and isolating *Trichuris suis* from said stool.

4. The method of claim 2, wherein the step of isolating *Trichuris suis* comprises removing a tissue from said preparatory animal, and isolating *Trichuris suis* or its eggs from said tissue.

5. The method of claim 4, wherein said tissue is intestines.

6. The method of claim 4, wherein the step of isolating *Trichuris suis* further comprises the steps of:

a) dissecting the tissue from said preparatory animal to allow for macroscopical isolation of worms to produce a worm culture wherein the worms lay eggs, b) filtering the worm culture to produce a filtrate with eggs; and c) isolating the eggs from said filtrate, thereby extracting eggs from said *Trichuris suis* isolate.

7. The method of claim 1, wherein for step d) the *Trichuris suis* eggs are developed from un-embryonated eggs into fully embryonated eggs.

8. The method of claim 1, wherein in step d) the embryonation of the *Trichuris suis* eggs is progressed until the embryonation coefficient (percentage of undifferentiated eggs developed into eggs containing larvae) is at least 60%.

9. The method of claim 2, wherein step a) is followed by the step aa) filtering the isolated material to reduce particle contamination and eggs of foreign pig parasites.

10. The method of claim 1, wherein step aa) is followed by the step aaa) floating the isolated material to reduce particle contamination.

11. The method of claim 1, wherein the sulphuric acid, $H_2SO_4$, used for washing and storing the isolated eggs in steps b) and c) and being used for the development of the eggs in step d) has a pH value in the range of 0-5, and wherein the sulphuric acid, $H_2SO_4$, used for storing the isolated and embryonated eggs in step e) has a pH value in the range of 0-5.

12. The method of claim 1, wherein the sulphuric acid, $H_2SO_4$, used for washing and storing the isolated eggs in steps b) and c) and being used for the development of the eggs in step d) has a pH value in the range of 0-4, and wherein the sulphuric acid, $H_2SO_4$, used for storing the isolated and embryonated eggs in step e) has a pH value in the range of 0-4.

13. The method of claim 1, wherein the sulphuric acid, $H_2SO_4$, used for washing and storing the isolated eggs in steps b) and c) and being used for the development of the eggs in step d) has a pH value in the range of 0-3, and wherein the sulphuric acid, $H_2SO_4$, used for storing the isolated and embryonated eggs in step e) has a pH value in the range of 0-3.

14. The method of claim 1, wherein the sulphuric acid, $H_2SO_4$, used for washing and storing the isolated eggs in steps b) and c) and being used for the development of the eggs in step d) has a pH value in the range of 0-2, and wherein the sulphuric acid, $H_2SO_4$, used for storing the isolated and embryonated eggs in step e) has a pH value in the range of 0-2.

15. The method of claim 2, wherein in step f) the embryonation of the *Trichuris suis* eggs is progressed until the embryonation coefficient (percentage of undifferentiated eggs developed into eggs containing larvae) is at least 60%.

16. The method of claim 2, wherein the liquid carrier sulphuric acid, $H_2SO_4$, used for washing and storing the un-embryonated eggs in steps d) and e) and being part of the composition in steps f) and further being used for storing the embryonated eggs in step g) has a pH value in the range of 0-5.

17. The method of claim 2, wherein the liquid carrier sulphuric acid, $H_2SO_4$ used for washing and storing the un-embryonated eggs in steps d) and e) and being part of the composition in steps f) and further being used for storing the embryonated eggs in step g) has a pH value in the range of 0-4.

18. The method of claim 2, wherein the liquid carrier sulphuric acid, $H_2SO_4$ used for washing and storing the un-embryonated eggs in steps d) and e) and being part of the composition in steps f) and further being used for storing the embryonated eggs in step g) has a pH value in the range of 0-3.

19. The method of claim 2, wherein the liquid carrier sulphuric acid, $H_2SO_4$ used for washing and storing the un-embryonated eggs in steps d) and e) and being part of the composition in steps f) and further being used for storing the embryonated eggs in step g) has a pH value in the range of 0-2.

20. The method of claim 1, wherein the embryonation process of step d) is followed by step dd) comprising washing the embryonated eggs in 2-10° C. sulphuric acid, H2S04, having a pH of below 6.

21. The method of claim 2, wherein the embryonation process of step f) is followed by step ff) comprising washing the embryonated eggs in 2-10° C. sulphuric acid, H2S04, having a pH of below 6.

* * * * *